US005239356A

United States Patent [19]

Holländer et al.

[11] Patent Number: 5,239,356

[45] Date of Patent: Aug. 24, 1993

[54] CONDENSATION NUCLEUS COUNTER

[75] Inventors: Werner Holländer, Celle; Wilhelm Dunkhorst, Petershagen; Hubert Lödding, Lehrte, all of Fed. Rep. of Germany

[73] Assignee: Fraunhofer-Gesellschaft zur Forderung der angewandten Forschung eV, Fed. Rep. of Germany

[21] Appl. No.: 908,845

[22] Filed: Jul. 1, 1992

Related U.S. Application Data

[63] Continuation of Ser. No. 716,805, Jun. 19, 1991, abandoned.

[30] Foreign Application Priority Data

Jun. 20, 1990 [DE] Fed. Rep. of Germany ....... 4019676

[51] Int. Cl.$^5$ ........................ G01N 1/00; G01N 15/14

[52] U.S. Cl. .................................... 356/37; 250/222.2

[58] Field of Search ........................ 356/37; 250/222.2

[56] References Cited

U.S. PATENT DOCUMENTS 4,790,650 12/1988 Keady .................................. 356/37

*Primary Examiner*—Vincent P. McGraw

*Assistant Examiner*—K. P. Hantis

*Attorney, Agent, or Firm*—Evenson, McKeown, Edwards & Lenahan

[57] ABSTRACT

A condensation nucleus counter has a humidifier zone, through which the sample air is guided, and an approximately perpendicularly arranged condensation zone, as well as an optical detection system with a light source and detector. The humidifying zone has a duct made of a permeable material and a hollow space surrounding this duct, the hollow space being used for receiving the process fluid. The condensation zone has a duct which, in turn, has a hollow space used for receiving the coolant. The condensation zone is connected with the humidifying zone by a connection piece.

15 Claims, 2 Drawing Sheets

CONDENSATION NUCLEUS COUNTER

This is a continuation of application Ser. No. 07/716,805, filed Jun. 19, 1991 now abandoned.

BACKGROUND AND SUMMARY OF THE INVENTION

The present invention relates to a condensation nucleus counter and its use.

In view of the high demands of modern clean-room technology, the need to detect particles of a diameter of <0.1 mm in gases is increasing constantly. The only method which allows the detection of particles already in the nanometer range consists of enlarging the particles by the condensation of steam in such a manner that they can be measured in another, for example, optical manner.

A typical apparatus of this type is the Model 3760 condensation nucleus counter of the firm Thermo System INC, Minneapolis, Minn. This nucleus counter comprises a humidifier zone as well as a condensation zone, the condensation zone being arranged at a right angle with respect to the humidifier zone. A duct, through which sample air is guided, leads through the humidifying zone and the condensation zone. The humidifying of the sample air in the condensation zone takes place by guiding the sample air over a humidifying bath containing the process liquid. In order to achieve a relatively high mass flow, the nucleus counter of the prior art provides a tube system which divides the mass flow into identical partial flows. The mass flow achieved in this manner amounts to 1.4 liters/min.

It is a disadvantage of the nucleus counter of the firm Thermo System that, despite expensive constructive measures, it can receive only a mass flow of 1.4 liters per minute. For measurements, as they are required today in modern clean-room technology, a mass flow of this type is too low. It is also a disadvantage that sealing problems occur, and a loss of particles is also possible.

From the German Patent Document DE-GM 73 21 827, a nucleus counter is known which has a humidifying zone consisting of a permeable material.

A disadvantage of the nucleus counter according to the German Patent Document No. DE-GM 73 21 827 is that, in the case of multiple measurements, i.e., when measurements are to be made at several measuring points simultaneously, in each case, individual apparatuses are required, that is, individual nucleus counters with all necessary peripheral equipment. This results in high expenditures with respect to equipment and cost.

It is therefore an object of the invention to provide a nucleus counter which permits the measuring of larger mass flows and the carrying-out of a measurement simultaneously at various points with relatively low expenditures with respect to equipment.

This and other objects are achieved by the present invention which provides a condensation nucleus counter comprising a humidifying zone having a first duct of a permeable material, through which sample air is guided, the first duct being surrounded by a hollow space that receives humidifying liquid. A condensation zone is arranged approximately perpendicularly with respect to the first duct, the condensation zone including a second duct which is surrounded by a hollow space which receives a coolant. A connection piece fluidly couples the condensation zone with the humidifying zone. The nucleus counter also has an optical detection system including a light source and a detector.

It is particularly advantageous for the duct of the humidifying zone to have a ring-shaped cross-section. However, the ring-shaped cross-section is only a preferred embodiment. Other shapes, such as elliptic or rectangular shapes, are just as suitable for the nucleus counter according to the invention.

It is advantageous for the permeable material to have a porous structure, such as sintered bodies, foams, nonwovens or the like. A sintered material with a wall thickness of from 3–15 mm is particularly preferred, in which case the construction with the wall thickness of from 3–8 mm is preferred. This duct made of the permeable material will then be used for the aerodynamic separation of the individual aerosol flows. This duct also dips into the process liquid which, as a result of capillary forces, penetrates through the porous material and thus provides a permanent feeding of liquid. The losses of the process liquid are compensated by a supply from the outside.

On the other hand, the porous material should be so fine-grained that, despite the hydrostatic excess pressure existing from the outside, the humidifier duct will not fill up with liquid. The size of the wall thickness therefore depends on the material and is generally between 2 and 15 mm. Preferably, it is between 3–8 mm. The geometrical dimensioning of the humidifying zone, in this case, should be such that a complete humidification of the aerosol flow is ensured. This will exist when the non-dimensional parameter A from $D \times T/a^2$ is in the range of approximately between 0.5 and 1.5. It is preferable for the parameter to reach the magnitude of 1. In this case, D is the diffusion coefficient of the process steam in the carrier gas; T is the dwell time of the aerosol volume in the humidifier; and a is a typical dimension of the humidifier transversely to the flow direction, thus, for example, in the case of a circular tube, the tube radius. The condensation zone is constructed in the same manner. The dimensioning of the condenser takes place analogously, the temperature conductivity of the carrier gas (K) now replacing the process steam diffusion coefficient, and the numerical value of parameter B being in the range of between 0.05 and 0.4, so that the condensation nuclei will have sufficient time for growing into sufficiently large droplets, and excessive steam will not condense on the wall. The value of B should preferably be between 0.1 and 0.3.

Preferably, the duct of the condensation zone has a special construction. It is advantageous in this case to use a tube with a circular cross-section, the tube tapering, following the transition area, starting from the connection piece to the transition area to the adapter. In the simplest case, this may take place for a pressing-together of a tube, such as a copper tube. The tube will then preferably have an elliptic cross-section. An optimal growth of the droplets is achieved by means of this construction of the condensation duct. It is also advantageous for the lens system to be connected with the duct of the condensation zone by an adapter which is constructed such that the grown particles can be supplied to the lens system without any losses. The adapter preferably has a conical structure. In order to ensure a constant mass flow, the sample gas is sucked through by means of a pump, a critical nozzle being connected in front of the pump.

Preferably, it is now also possible to combine several individual measuring ducts to form a nucleus counter unit. This is implemented by the fact that for all ducts of the humidifying zone as well as of the condensation zone, only a single process bath or a single cooling device is provided. The housing of the humidifying zone therefore surrounds not only a single measuring duct but all measuring ducts of a measuring unit. In the same manner, the housing of the condensation zone surrounds all ducts of the cooling zone. As a result of this advantageous development, only one heating bath and one cooling device are required for the whole measuring unit. Likewise, only one pump is necessary for the whole system. As a result, the operating and constructive expenditures are lowered drastically and multiple measurements are made possible at the same time.

Other objects, advantages and novel features of the present invention will become apparent from the following detailed description of the invention when considered in conjunction with the accompanying drawings.

DETAILED DESCRIPTION OF THE DRAWINGS

Figure 1:
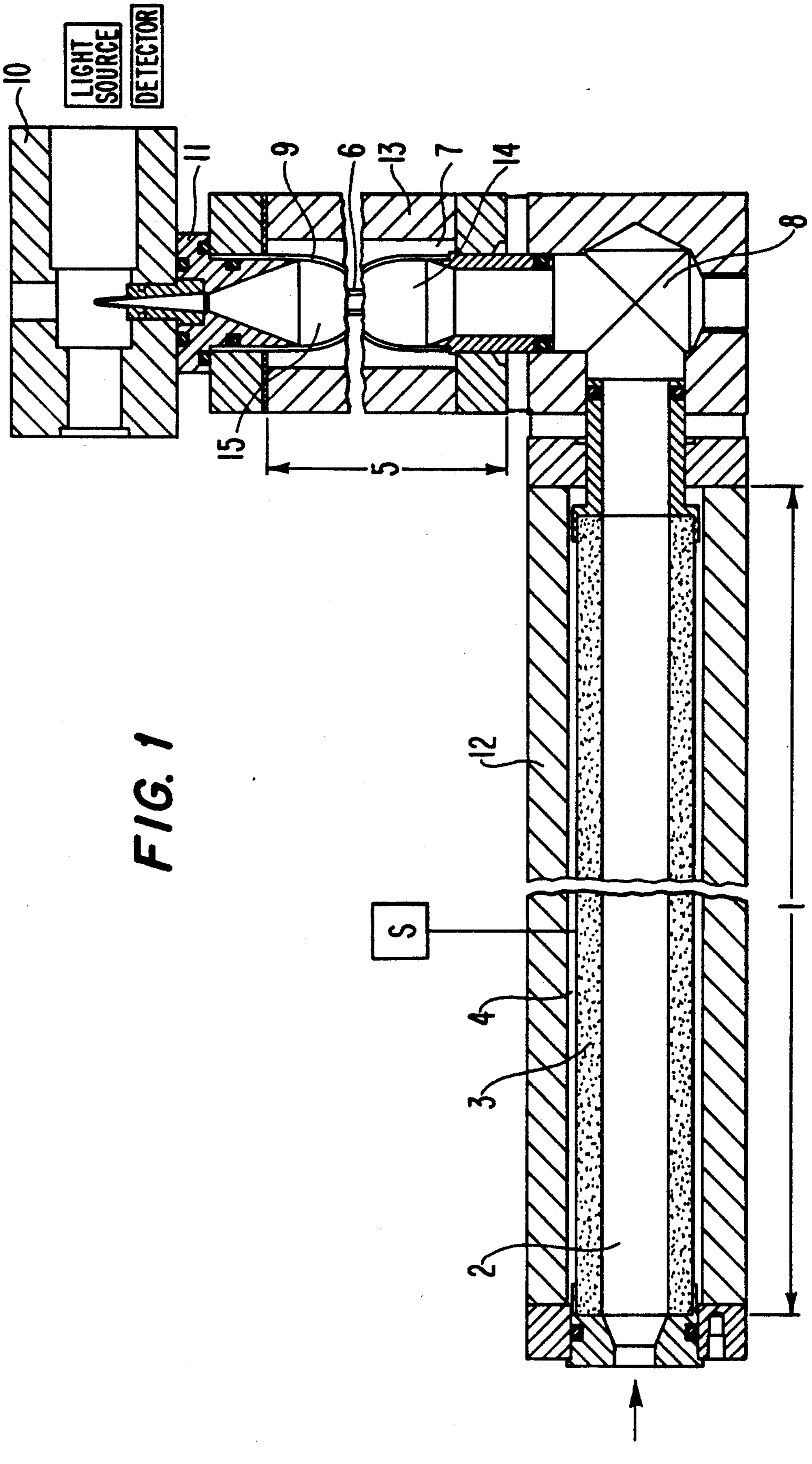
FIG. 1 shows a sectional view of the condensation nucleus counter constructed according to an embodiment of the present invention.

The nucleus counter constructed according to an embodiment of the present invention is shown in FIG. 1. The following describes this counter and its use. In this embodiment of the invention, the particle-containing gas current enters into the duct 2 of the humidifying zone 1. The duct 2 of the humidifying zone 1 is constructed in such a manner that, although, on the one hand, the particles are not lost by diffusion, on the other hand, the carrier gas flow is saturated with the process steam at the saturation temperature. This is achieved in that the duct 2 of the humidifying zone 1 has a porous structure 3 which has sufficient permeability for the respective process liquid. The permeable material 3 has a porous structure, and has a wall thickness of from 3 to 15 mm, and can be a sintered material. A preferred wall thickness of the sintered material is 3 to 8 mm.

The humidifying liquid is selected from the group of perfluoroalkanes or higher alcohols, and can be, for example, n-butanol. Also, the humidifying liquid can be supplemented by an external supply indicated schematically in FIG. 1 with reference 5.

The process liquid is situated in the hollow space 4 and enters into the interior of the humidifying duct 2 as a result of capillary forces. The hollow space 4, in which the process liquid is situated, is surrounded by a housing 12. This housing may, for example, be manufactured from aluminum. In this case, the geometrical dimensioning of the humidifying zone must take place in such a manner that the non-dimensional parameter A given by the relationship $D \times T/a^2$ is in the range of between 0.5–1.5.

When this prerequisite exists, a complete humidification of the aerosol flow is ensured. In this case, D is the diffusion coefficient of the process steam in the carrier gas; T is the dwell time of the aerosol volume in the humidifier; and a is a typical dimension of the humidifier transversely to the flow and to the flow direction, for example, the radius in the case of a circular tube. Because of this construction, mass flows of sample air of different sizes can be taken in, depending on the dimensioning of the tube. In some preferred embodiments, the parameter A is equal to 1. In certain embodiments, the diameter of the duct 2 of the humidifying zone 1 is dimensioned such that a mass flow of up to 6 liters of sample air are receivable per minute, although in other embodiments, only up to 3 liters of sample air are receivable per minute.

The completely saturated sample air will then be deflected by way of the connection piece 8 and guided into a condensation zone 5.

It is particularly important that no sealing problems occur between the humidifying zone 1 and the connection piece 8 when the humidifying zone 1 is connected with the connection piece 8 via a teflon O-ring. The same situation exists with the connection between the connection piece 8 and the condensation zone 5.

The saturated gas enters into the condensation zone 5 and is cooled in the process so that a strong oversaturation is generated because the saturation steam pressure decreases considerably when the temperature falls, but the momentary steam particle pressure still corresponds to the high saturation steam pressure in the saturator. The duct 6 is geometrically dimensioned such that the non-dimensional parameter B, which is a result of the relationship $K \times T/a^2$, is in the range of between 0.05 to 0.4, where T is the dwell time of the aerosol volume in the second duct 6 and a is a typical dimension of the second duct 6 transversely to the flow direction and K is the temperature conductivity of the carrier gas. Selecting the parameter B to be in the range of between 0.05 and 0.4 results in the particles growing to a size that is sufficient for being counted optically in the detection chamber which follows.

The duct 6 of the condensation zone 5 includes a tube 9 which tapers behind a transition area 14 originating from the connection piece 8 toward another transition area 15.

In this case the cooling is achieved by introducing a coolant from a cooling bath in the circulation through the hollow space 7 of the condensation zone 5. The hollow space 7 of the condensation zone 5, in turn, is surrounded by a housing 13.

The mass flow with the grown particles is now guided to a lens system 10 via an adapter 11. The adapter 11 is designed such that no losses occur during the transition, achieved by its conical design. The particles are then counted in a conventional lens system which may comprise a laser and a photodetector. By means of a pump connected to the apparatus, the mass flow of the sample gas is adjusted to an appropriate size during the whole measuring operation. It was found to be advantageous for a critical nozzle to be connected in front of the pump.

Figure 2:
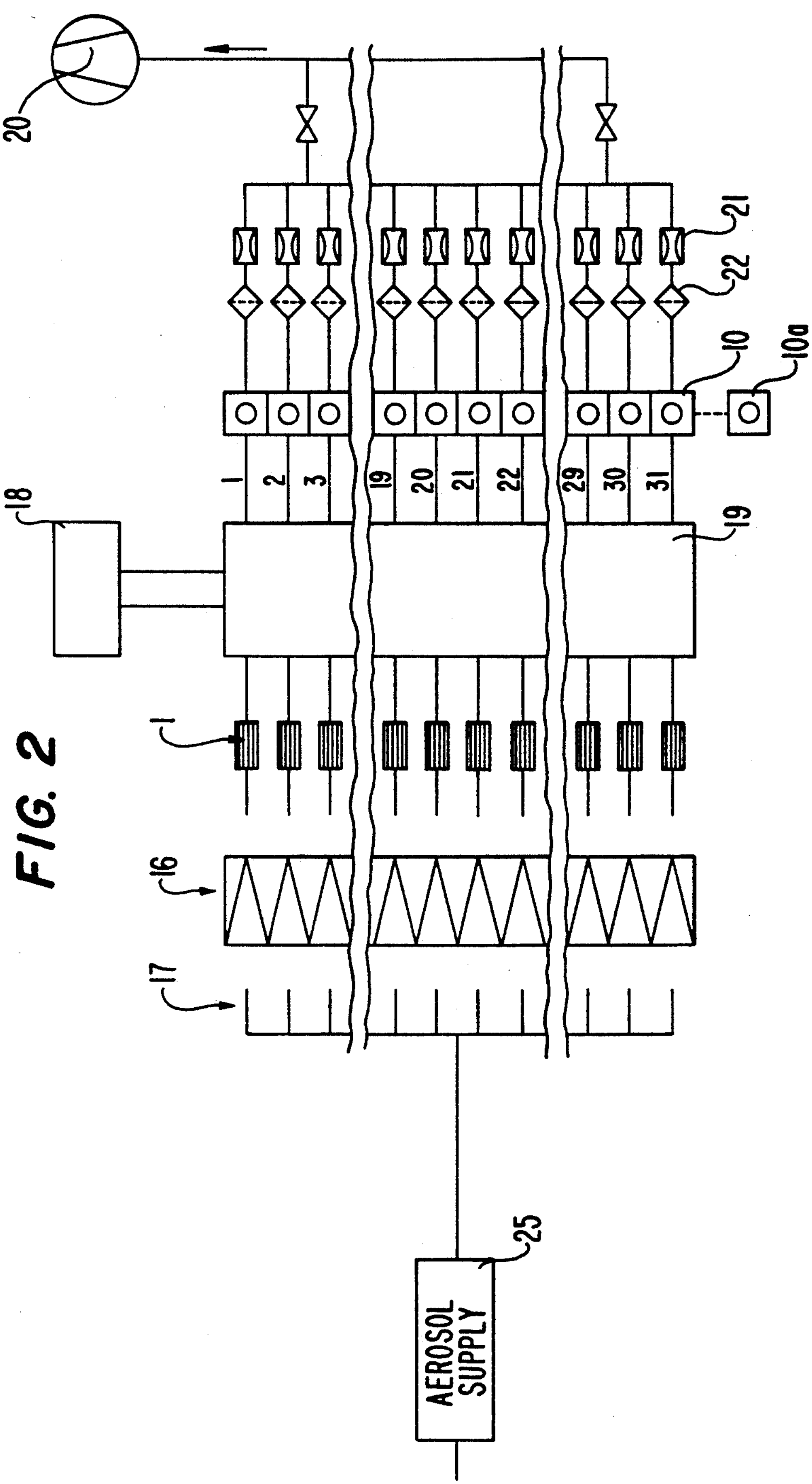
FIG. 2 shows the multiple use of a locally disintegrated penetration measuring on filter bags.

FIG. 2 shows a locally disintegrated penetration measuring on filter bags as an example of a multiple measuring. Condensation counters of the prior art are constructed to be completely discrete with respect to their components so that each nucleus counter has its own humidifying zone, its own saturator temperature bath, its own condensation zone with separate cooling, a separate lens system and individual pumps. This can be avoided by means of the nucleus counter of the present invention because, as a result of its construction, it is now possible to surround all ducts of the humidifying zone by a single evaporation bath, because the ducts are made of a porous material. FIG. 2 shows such a measuring arrangement of a locally disintegrated penetration measuring on filter bags. In this example, all filters 16 are to be tested for their transmittance. For this purpose, all of the filters 16 are uniformly acted upon by a testing aerosol via a distributor system 17 connected to an aerosol supply 25. One humidifying zone 1 respectively will then always be connected behind each individual filter 16. For these, for example, thirty-one humidifying zones 1 (i.e. humidifiers), only a single humidifier bath is required and therefore also only one evaporating unit.

The individually divided mass flows are then guided to the condensation zone, this condensation zone being supplied by only one cooling bath 19 which is controlled by a thermostat 18. The cooling bath 19 is shown in FIG. 2 as surrounding the thirty-one condensation zones 5. In the present example, each individual nucleus counter has its own optical detection system 10, comprising a light source and a detector. However, it is also possible to make available only one light source for all individual measurements as indicated by the single light source 10*a* in FIG. 2. The mass flow is controlled by a pump 20 and critical nozzles 21 as well as filters 22. As a result, the most varied multiple measurements can be carried out by means of such a nucleus counting unit. The number of individual nucleus counters is adapted to the respective objectives. Likewise, by means of a corresponding design of the duct cross-section, the mass flow can be adapted.

As a result of the nucleus counter according to the invention, a nucleus counter is provided which without any high expenditures can be adapted to the respective problem.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A condensation nucleus counter comprising:

a humidifying zone having a first duct of a permeable material through which sample air is guided, the first duct being surrounded by a hollow space that receives humidifying liquid;

a condensation zone arranged approximately perpendicularly with respect to said first duct, the condensation zone including a second duct which is surrounded by a hollow space which receives a coolant;

a connection piece which fluidly couples the condensation zone with the humidifying zone;

an optical detection system including a light source and a detector;

wherein the first duct of the humidifying zone has a ring-shaped cross-section;

wherein the permeable material has a porous structure, and has a wall thickness of from 3 to 15 mm.

2. A nucleus counter according to claim 1, wherein the permeable material is a sintered material.

3. A nucleus counter according to claim 1, wherein the first duct is geometrically dimensioned such that a non-dimensional parameter A, which is a result of a relationship $D \times T/a^2$, is in the range of approximately 0.5 to 1.5, wherein D is the diffusion coefficient of the process steam in the carrier gas, T is the dwell time of aerosol volume in the first duct and a is a typical dimension of the first duct transversely to a flow direction.

4. A nucleus counter according to claim 3, wherein the first duct is a circular tube and a is the tube radius.

5. A nucleus counter according to claim 3, wherein the parameter A is equal to 1.

6. A nucleus counter according to claim 4, wherein the diameter of the first duct of the humidifying zone is dimensioned such that a mass flow of up to 6 liters of sample air are receivable per minute.

7. A nucleus counter according to claim 4, wherein the diameter of the duct of the humidifying zone is dimensioned such that up to 3 liters of sample air are receivable per minute.

8. A nucleus counter according to claim 1, wherein the second duct is geometrically dimensioned such that a non-dimensional parameter B, which is a result of a relationship $K \times T/a^2$, is between 0.05 to 0.4, where T is the dwell time of aerosol volume in the second duct and a is a typical dimension of the second duct transversely to a flow direction and K is the temperature conductivity of a carrier gas.

9. A nucleus counter according to claim 1, further comprising at least 2 individual measuring ducts, each measuring duct having the first duct of the humidifying zone that is connected via the connection piece with the second duct of the condensation zone, the individual measuring ducts forming a nucleus counter unit.

10. A nucleus counter according to claim 9, wherein the hollow space of the humidifying zones as well as the hollow space of the condensation zones of the nucleus counter unit are each surrounded by a single housing.

11. A nucleus counter according to claim 10, each individual measuring duct, has a separate optical detection system with a light source and a detector.

12. A nucleus counter according to claim 9, wherein all of the individual measuring ducts are connected with a single light source.

13. A nucleus counter according to claims 9, further comprising a single pump coupled to all of the individual measuring ducts are connected with a single pump for controlling mass flow.

14. A nucleus counter according to claim 13, further comprising a critical nozzle connected in front of the pump for stabilizing of the mass flow.

15. A nucleus counter according to claim 9, wherein said nucleus counter performs locally disintegrated measuring of the penetration on at least one of filter bags or in clean rooms.

* * * * *